United States Patent
Hiyoshi et al.

(10) Patent No.: US 7,820,861 B2
(45) Date of Patent: Oct. 26, 2010

(54) 2-METHOXYMETHYLPHENYLHYDRAZINE

(75) Inventors: Hidetaka Hiyoshi, Shizuoka (JP); Mahito Ogawa, Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 783 days.

(21) Appl. No.: 11/790,940

(22) Filed: Apr. 30, 2007

(65) Prior Publication Data

US 2007/0213561 A1   Sep. 13, 2007

Related U.S. Application Data

(62) Division of application No. 11/442,970, filed on May 31, 2006, now Pat. No. 7,521,555, which is a division of application No. 10/398,025, filed as application No. PCT/JP01/09040 on Oct. 15, 2001, now Pat. No. 7,271,263.

(30) Foreign Application Priority Data

Oct. 17, 2000   (JP)   .............. 2000-316345
Feb. 9, 2001   (JP)   .............. 2001-034216

(51) Int. Cl.
*C07C 241/00* (2006.01)
*C07C 243/00* (2006.01)
*C07C 249/00* (2006.01)
*C07C 251/00* (2006.01)
*C07D 239/02* (2006.01)

(52) U.S. Cl. ........................ 564/310; 544/319

(58) Field of Classification Search .............. None
See application file for complete search history.

(56) References Cited

U.S. PATENT DOCUMENTS 6,458,748 B1   10/2002   Yoshimura et al.

FOREIGN PATENT DOCUMENTS

| JP | 11-60562 | 3/1999 |
| JP | 2000-44546 | 2/2000 |
| JP | 2000-63360 | 2/2000 |
| WO | 00/06553 | 10/2000 |

OTHER PUBLICATIONS

Gannett et al. Chem. Res. Toxicol. 1997, 10, 1372-1377.*
Archer et al, Quinazolines and 1, 4-benzodiazepines, 82.5-Pyrimidyl-and 5-pyrazinylbenzodiazepines, J. Med. Chem. (1977).
Takai et al, Chemical and Pharmaceutical Bulleting, vol. 34, No. 5, 1986, pp. 1907-1916.
Ockenden et al, Journal of the Chemical Society, 1953, pp. 612-618.
Sternback et al, Journal of Organic Chemistry, vol. 26, No. 11, 1961, pp. 4488-4497.
Gribble et al., Journal of Organic Chemistry, vol. 36, No. 18, 1971, pp. 2724-2727.

* cited by examiner

*Primary Examiner*—Daniel M Sullivan
*Assistant Examiner*—Clinton Brooks
(74) *Attorney, Agent, or Firm*—Bacon & Thomas, PLLC

(57) ABSTRACT

A substitute aniline compound represented by the following formula (6):

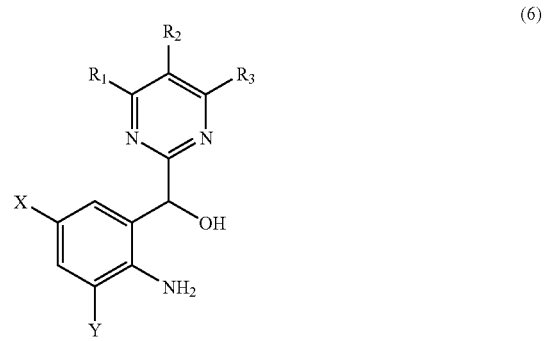

(6)

wherein, $R_1$, $R_2$ and $R_3$ are each independently an alkyl group, an alkoxy group, an alkoxyalkyl group, a haloalkyl group, a carboxyl group, an alkoxycarbonyl group, an alkyl-carboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or halogen. A process for producing the compound formula (6) is also discussed.

1 Claim, No Drawings

2-METHOXYMETHYLPHENYLHYDRAZINE

TECHNICAL FIELD

The present invention relates to a process for producing a substituted aniline compound which may become a useful intermediate in production of, for example, agricultural chemicals and medicines.

BACKGROUND ART

It is already known that some of sulfonanilide derivatives having 4,6-dimethoxypyrmidine have a high herbicidal activity (see JP-A-11-60562 and WO00/06553). It is also known that, in production thereof, a substituted aniline compound is useful as an important intermediate.

Meanwhile, processes for producing a substituted aniline compound which is an important intermediate for sulfonanilide derivative having a high herbicidal activity, are disclosed (see JP-A-7-48359, WO96/41799). These processes each utilize a reaction which is disadvantageous in industrial application; therefore, it has been desired to develop a process which can produce an intended substituted aniline advantageously in industry.

DISCLOSURE OF THE INVENTION

The present inventor made a study in order to solve the above problem. As a result, it was found out that an intended substituted aniline compound can be produced by reacting, for example, a (pyrimidine-2-yl)-2-propanone compound with a hydrazine compound in the presence of an acid to produce a substituted indole compound, oxidizing the substituted indole compound to give rise to the ring opening of indole ring to obtain an acetanilide compound, and subjecting the acetanilide compound to reduction preferably with sodium borohydride or to deacetylation of the amide moiety, that is, the above problem can be solved. The finding has led to the completion of the present invention.

BEST MODE FOR CARRYING OUT THE INVENTION

The present invention is described in detail below.
Herein, the above problem has been solved by providing mainly the following inventions [1] to [14].

[1] A process for producing a substituted aniline compound represented by the following general formula (6):

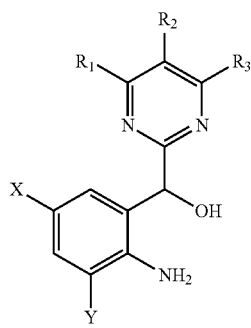

(6)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or a halogen atom), characterized by oxidizing a substituted indole compound represented by the following general formula (3):

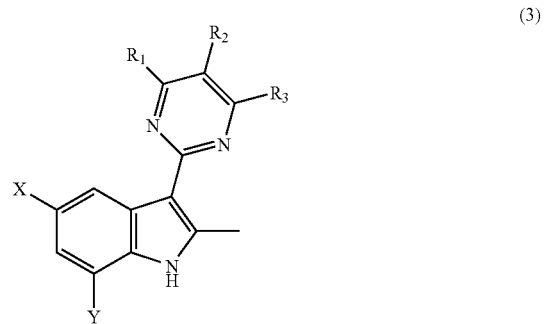

(3)

(in the formula, $R_1$, $R_2$, $R_3$, X and Y have the same definitions as given above) to give rise to the ring opening of indole ring to produce an acetanilide compound represented by the following general formula (4):

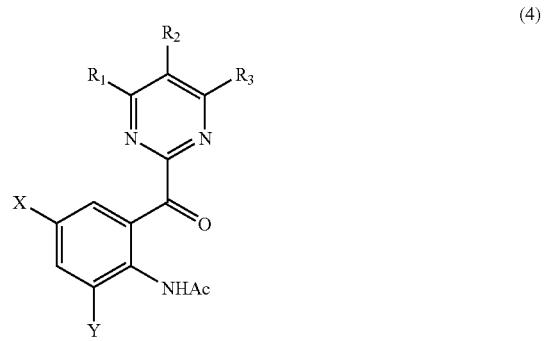

(4)

(in the formula, $R_1$, $R_2$, $R_3$, X and Y have the same definitions as given above; and Ac is an acetyl group) and subjecting this compound to reduction and deacetylation.

[2] A process for producing a substituted aniline compound represented by the following general formula (6):

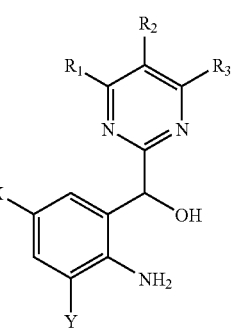

(6)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkyl-carboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or a halogen atom), characterized by oxidizing a substituted indole compound represented by the following general formula (3):

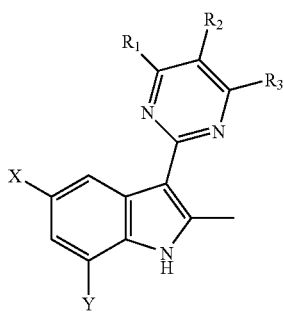

(3)

(in the formula, $R_1$, $R_2$, $R_3$, X and Y have the same definitions as given above) to give rise to the ring opening of indole ring to produce an acetanilide compound represented by the following general formula (4):

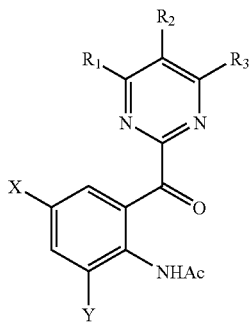

(4)

(in the formula, $R_1$, $R_2$, $R_3$, X and Y have the same definitions as given above; and Ac is an acetyl group), reducing this compound to produce a 2-(pyrimidine-2-ylhydroxymethyl) acetanilide compound represented by the following general formula (5):

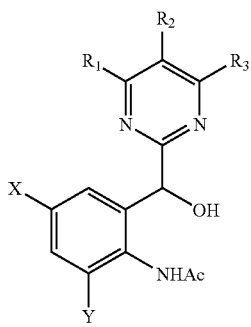

(5)

(in the formula, $R_1$, $R_2$, $R_3$, X, Y and Ac have the same definitions as given above) and successively conducting deacetylation.

[3] A process for producing a substituted aniline compound represented by the following general formula (6):

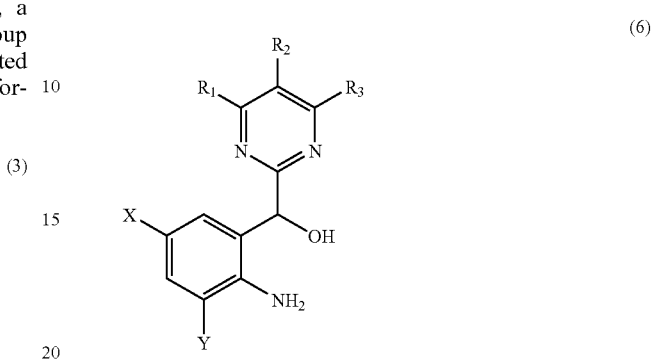

(6)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkyl-carboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or a halogen atom), characterized by oxidizing a substituted indole compound represented by the following general formula (3):

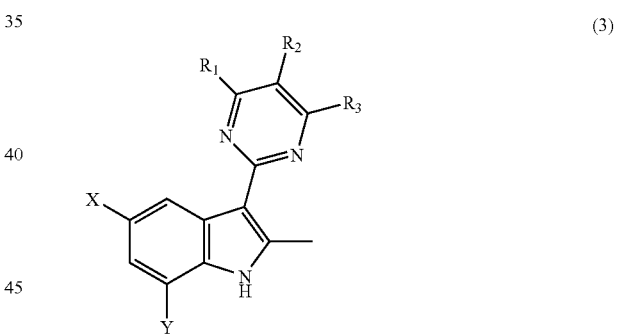

(3)

(in the formula, $R_1$, $R_2$, $R_3$, X and Y have the same definitions as given above) to give rise to the ring opening of indole ring to produce an acetanilide compound represented by the following general formula (4):

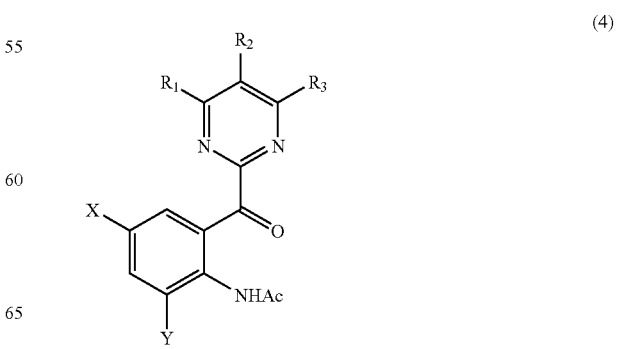

(4)

(in the formula, $R_1$, $R_2$, $R_3$, X and Y have the same definitions as given above; and Ac is an acetyl group), reducing this compound without isolation thereof to produce a 2-(pyrimidine-2-ylhydroxymethyl)acetanilide compound represented by the following general formula (5):

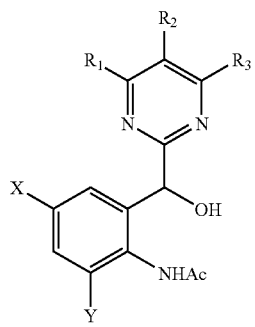

(5)

(in the formula, $R_1$, $R_2$, $R_3$, X, Y and Ac have the same definitions as given above) and successively conducting deacetylation.

[4] A process for producing a substituted aniline compound represented by the following general formula (6):

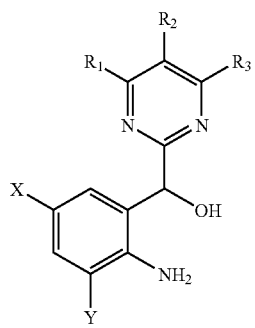

(6)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or a halogen atom), characterized by oxidizing a substituted indole compound represented by the following general formula (3):

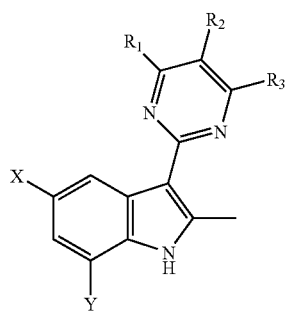

(3)

(in the formula, $R_1$, $R_2$, X and Y have the same definitions as given above) to give rise to the ring opening of indole ring to produce an acetanilide compound represented by the following general formula (4):

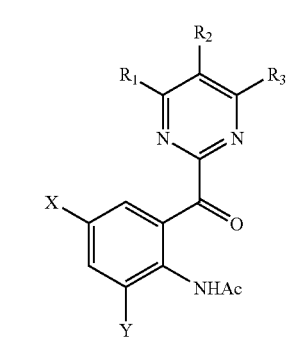

(4)

(in the formula, $R_1$, $R_2$, $R_3$, X and Y have the same definitions as given above; and Ac is an acetyl group), deacetylating this compound to produce an amino compound represented by the following general formula (7):

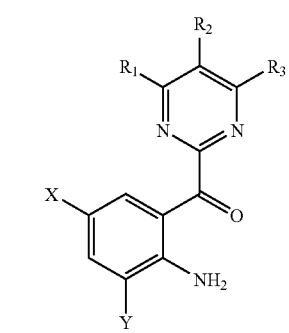

(7)

(in the formula, $R_1$, $R_2$, $R_3$, X and Y have the same definitions as given above) and successively conducting reduction.

[5] A process for producing a substituted aniline compound according to any of above 1 to 4, wherein the substituted indole compound represented by the following general formula (3):

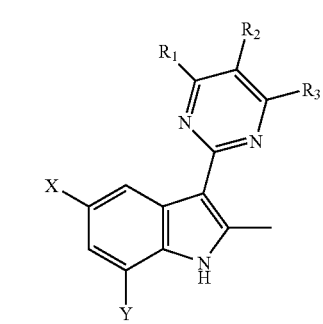

(3)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or a halogen atom) is produced by reacting, in the presence of an acid, a (pyrimidine-2-yl)-2-propanone compound represented by the following general formula (1):

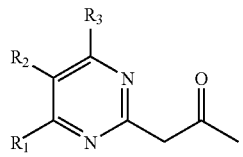

(1)

(in the formula, $R_1$, $R_2$ and $R_3$ have the same definitions as given above) with a hydrazine compound represented by the following general formula (2):

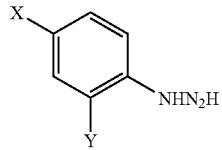

(2)

(in the formula, X and Y have the same definitions as given above).

[6] A process for producing an amino compound represented by the following general formula (7):

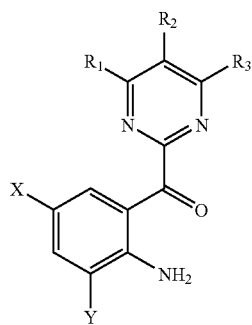

(7)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or a halogen atom), characterized by oxidizing a substituted indole compound represented by the following general formula (3):

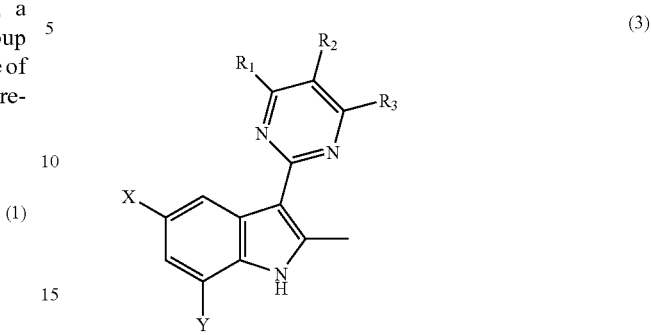

(3)

(in the formula, $R_1$, $R_2$, $R_3$, X and Y have the same definitions as given above) to give rise to the ring opening of indole ring to produce an acetanilide compound represented by the following general formula (4):

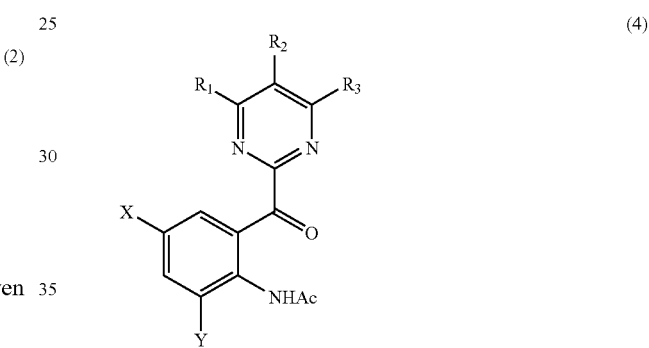

(4)

(in the formula, $R_1$, $R_2$, $R_3$, X and Y have the same definitions as given above; and Ac is an acetyl group) and deacetylating this compound.

[7] A process for producing a 2-(pyrimidine-2-ylhydroxymethyl)acetanilide compound represented by the following general formula (5):

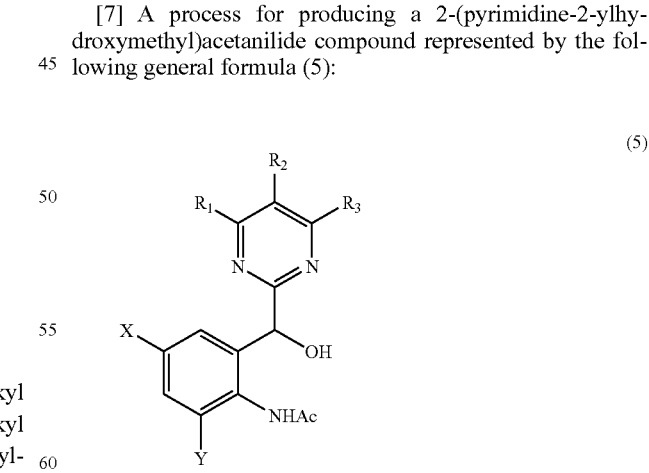

(5)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom;

X and Y are each independently a hydrogen atom, an alkyl group, an alkoxy group, an alkoxyalkyl group, a haloalkyl group, a carboxyl group, an alkoxycarbonyl group or a halogen atom; and Ac is an acetyl group), characterized by oxidizing a substituted indole compound represented by the following general formula (3):

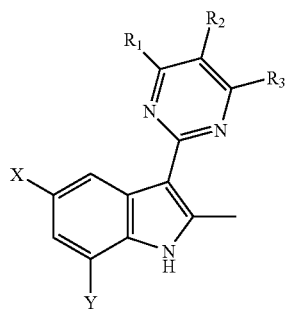

(3)

(in the formula, $R_1$, $R_2$, $R_3$, X and Y have the same definitions as given above) to give rise to the ring opening of indole ring to produce an acetanilide compound represented by the following general formula (4):

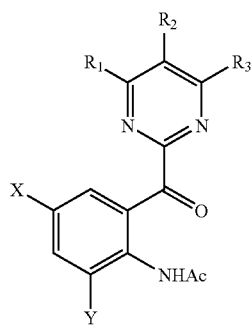

(4)

(in the formula, $R_1$, $R_2$, $R_3$, X and Y have the same definitions as given above; and Ac is an acetyl group) and reducing this compound.

[8] A process for producing a 2-(pyrimidine-2-ylhydroxymethyl)acetanilide compound represented by the following general formula (5):

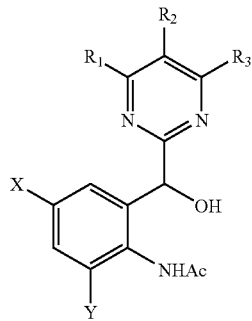

(5)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; X and Y are each independently a hydrogen atom, an alkyl group, an alkoxy group, an alkoxyalkyl group, a haloalkyl group, a carboxyl group, an alkoxycarbonyl group or a halogen atom; and Ac is an acetyl group), characterized by oxidizing a substituted indole compound represented by the following general formula (3):

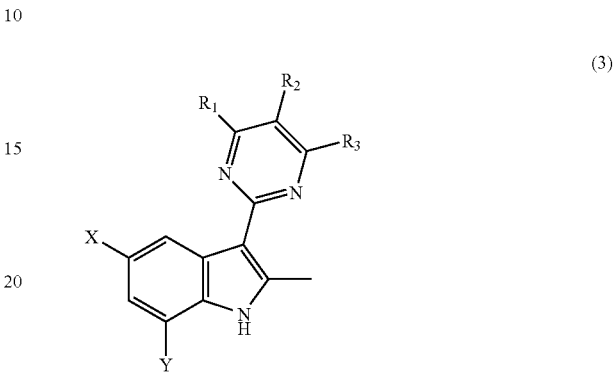

(3)

(in the formula, $R_1$, $R_2$, $R_3$, X and Y have the same definitions as given above) to give rise to the ring opening of indole ring to produce an acetanilide compound represented by the following general formula (4):

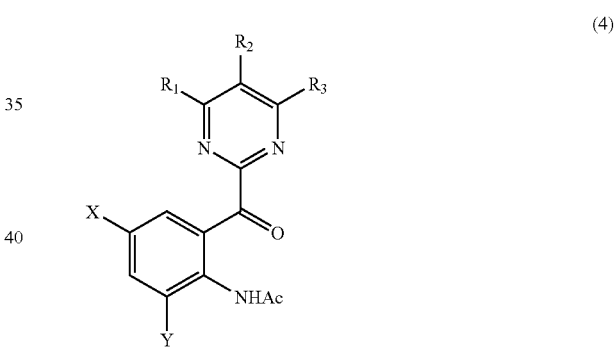

(4)

(in the formula, $R_1$, $R_2$, $R_3$, X, Y and Ac have the same definitions as given above) and reducing this compound without isolation thereof.

[9] A process for producing a substituted indole compound represented by the following general formula (3):

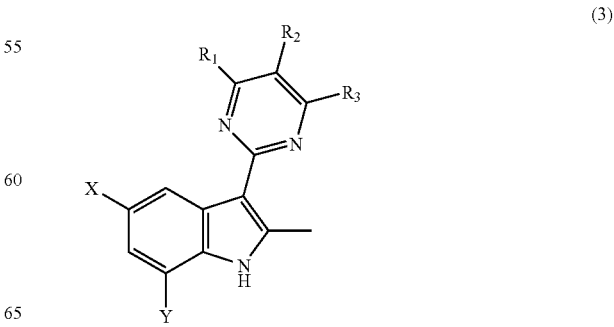

(3)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or a halogen atom), characterized by reacting, in the presence of an acid, a (pyrimidine-2-yl)-2-propanone compound represented by the following general formula (1):

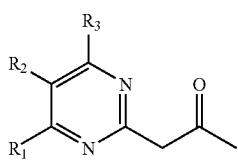
(1)

(in the formula, $R_1$, $R_2$ and $R_3$ have the same definitions as given above) with a hydrazine compound represented by the following general formula (2):

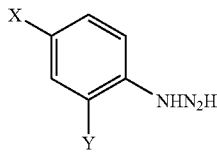
(2)

(in the formula, X and Y have the same definitions as given above).

[10] A process for producing an acetanilide compound represented by the following general formula (4):

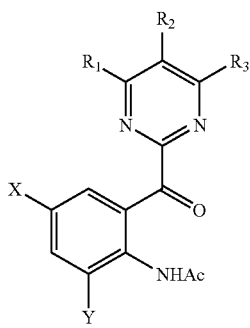
(4)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; X and Y are each independently a hydrogen atom, an alkyl group, an alkoxy group, an alkoxyalkyl group, a haloalkyl group, a carboxyl group, an alkoxycarbonyl group or a halogen atom; and Ac is an acetyl group), characterized by oxidizing a substituted indole compound represented by the following general formula (3):

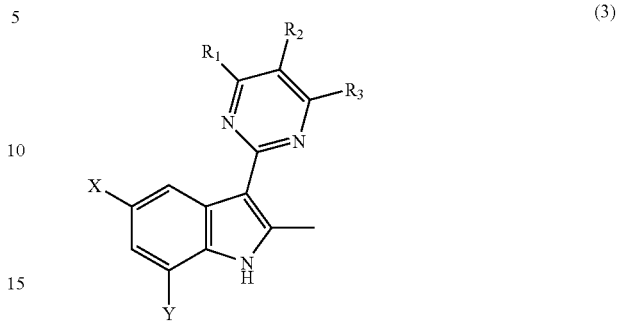
(3)

(in the formula, $R_1$, $R_2$, $R_3$, X and Y have the same definitions as given above) to give rise to the ring opening of indole ring.

[11] A process for producing an amino compound represented by the following general formula (7):

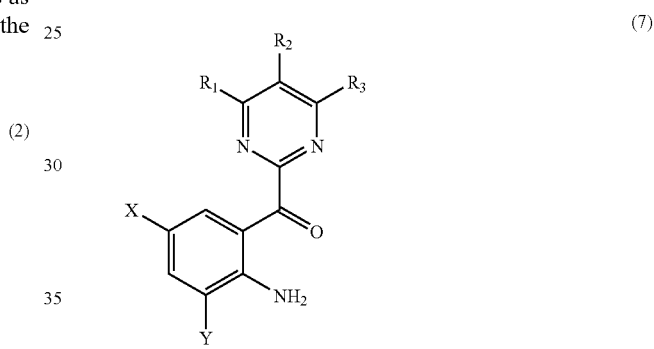
(7)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or a halogen atom), characterized by deacetylating an acetanilide compound represented by the following general formula (4):

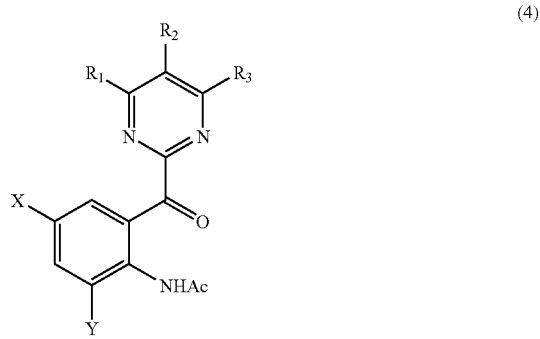
(4)

(in the formula, $R_1$, $R_2$, $R_3$, X and Y have the same definitions as given above; and Ac is an acetyl group).

[12] A process for producing a substituted aniline compound represented by the following general formula (6):

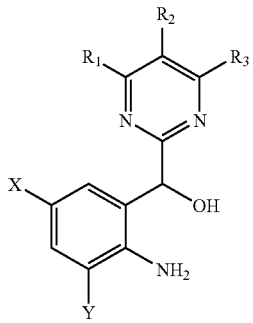

(6)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or a halogen atom), characterized by reducing an amino compound represented by the following general formula (7):

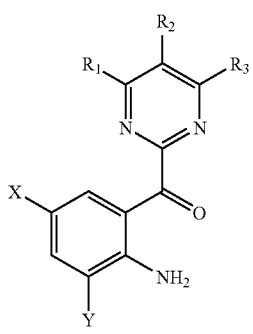

(7)

(in the formula, $R_1$, $R_2$, $R_3$, X and Y have the same definitions as given above).

[13] A process for producing a 2-(pyrimidine-2-ylhydroxymethyl)acetanilide compound represented by the following general formula (5):

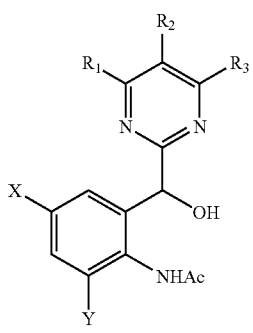

(5)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; X and Y are each independently a hydrogen atom, an alkyl group, an alkoxy group, an alkoxyalkyl group, a haloalkyl group, a carboxyl group, an alkoxycarbonyl group or a halogen atom; and Ac is an acetyl group), characterized by reducing an acetanilide compound represented by the following general formula (4):

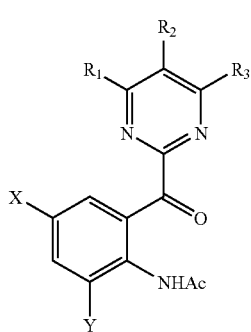

(4)

(in the formula, $R_1$, $R_2$, $R_3$, X, Y and Ac have the same definitions as given above).

[14] A process for producing a substituted aniline compound represented by the following general formula (6):

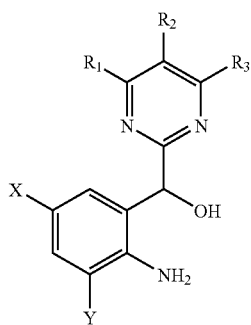

(6)

(in the formula, $R_1$, $R_2$ and $R_3$ are each independently an alkyl group, an alkoxy group, an alkoxyalkyl group, a haloalkyl group, a carboxyl group, an alkoxycarbonyl group, an alkylcarboxamide group, a nitro group, an aryl group, an arylalkyl group, an aryloxy group, a halogen atom or a hydrogen atom; and X and Y are each independently a hydrogen atom, an alkyl group, an alkoxy group, an alkoxyalkyl group, a haloalkyl group, a carboxyl group, an alkoxycarbonyl group or a halogen atom), characterized by deacetylating a 2-(pyrimidine-2-ylhydroxymethyl)acetanilide compound represented by the following general formula (5):

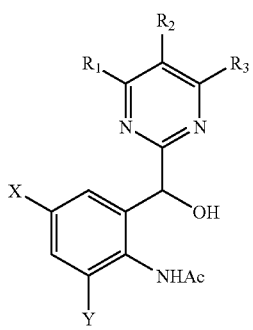

(5)

(in the formula, $R_1$, $R_2$, $R_3$, X and Y have the same definitions as given above; and Ac is an acetyl group).

The present invention is described in detail below.

The present invention process described in [1] (hereinafter, "the present invention process" has the same meaning unless otherwise specified) uses a substituted indole compound represented by the general formula (3), as a raw material. This substituted indole compound represented by the general formula (3) can be produced by reacting, in the presence of an acid, a (pyrimidine-2-yl)-2-propanone compound represented the general formula (1) with a hydrazine compound represented by the general formula (2). Hence, description is made first on a step (step 1) for producing the substituted indole compound represented by the general formula (3).

First, description is made on the (pyrimidine-2-yl)-2-propanone compound represented the general formula (1) and the hydrazine compound represented by the general formula (2) both used as raw materials.

In the (pyrimidine-2-yl)-2-propanone compound represented the general formula (1), $R_1$, $R_2$ and $R_3$ can be each independently a 1 to 6 carbon atoms (hereinafter, carbon atoms, when they are, for example, 1 to 6 carbon atoms, are abbreviated to "C1 to C6") straight chain or branched chain C1 to C6 alkyl group such as methyl group, ethyl group, n-propyl group, isopropyl group, n-butyl group, sec-butyl group, tert-butyl group, n-pentyl group, n-hexyl group or the like; a straight chain or branched chain C1 to C6 alkoxy group such as methoxy group, ethoxy group, n-propoxy group, isopropoxy group or the like; a straight chain or branched chain C1 to C6 alkoxy (C1 to C6) alkyl group such as methoxymethyl group, methoxy ethyl group, ethoxyethyl group or the like; a straight chain or branched chain C1 to C6 haloalkyl group such as fluoromethyl group, difluoromethyl group, trifluoromethyl group or the like; a carboxyl group; a straight chain or branched chain C1 to C6 alkoxycarbonyl group such as methoxycarbonyl group, ethoxycarbonyl group or the like; a straight chain or branched chain (C1 to C6 alkyl)carboxamide group such as methylcarboxamide group, ethylcarboxamide group or the like; a nitro group; an aryl group such as phenyl group or the like; a straight chain or branched chain aryl(C1 to C6)alkyl group such as phenylmethyl group, phenylethyl group or the like; an aryloxy group such as phenoxy group, naphthoxy group or the like; a halogen atom such as bromo group, chloro group, fluoro group, iodo group or the like; or a hydrogen atom.

Therefore, as the (pyrimidine-2-yl)-2-propanone compound represented the general formula (1) usable in the step 1, there can be specifically mentioned, for example, 1-(pyrimidine-2-yl)-2-propanone, 1-(4,6-dimethylpyrimidine-2-yl)-2-propanone, 1-(4,6-dimethoxypyrimidine-2-yl)-2-propanone, 1-(4,6-dimethoxy-5-methylpyrimidine-2-yl)-2-propanone, 1-(4,6-dimethoxy-5-ethylpyrimidine-2-yl)-2-propanone, 1-(4,6-dimethoxy-5-nitropyrimidine-2-yl)-2-propanone, 1-(4,6-dichloropyrimidine-2-yl)-2-propanone, 1-(4,6-dimethoxy-5-ethoxycarbonylpyrimidine-2-yl)-2-propanone, and 1-(4,6-diethoxypyrimidine-2-yl)-2-propanone. The (pyrimidine-2-yl)-2-propanone compound represented the general formula (1) has tautomers and any of the tautomers can be used in the present invention process. However, in the present specification, the structure of the compound is expressed as a 2-propanone derivative as seen in the general formula (1) and the naming of the compound is made as a 2-propanone derivative as seen above.

These (pyrimidine-2-yl)-2-propanone compounds represented the general formula (1) are known compounds, or compounds which can be produced from a raw material such as 2-phenylsulfonyl-4,6-dimethylpyrimidine or the like in accordance with, for example, the process described in Chemical & Pharmaceutical Bulletin, p. 152 (1982). The (pyrimidine-2-yl)-2-propanone compound represented by the general formula (1) includes novel compounds, for example, 1-(4,6-dimethoxypyrimidine-2-yl)-2-propanone and this compound is a raw material compound useful in production of the substituted aniline compound represented by the general formula (6).

Meanwhile, in the general formula (2), X and Y can be each independently a straight chain or branched chain C1 to C6 alkyl group such as methyl group, ethyl group, n-propyl group, isopropyl group, n-butyl group, sec-butyl group, tert-butyl group, n-pentyl group, n-hexyl group or the like; a straight chain or branched chain C1 to C6 alkoxy group such as methoxy group, ethoxy group, n-propoxy group, isopropoxy group or the like; a straight chain or branched chain C1 to C6 alkoxy (C1 to C6) alkyl group such as methoxymethyl group, methoxyethyl group, ethoxyethyl group or the like; a straight chain or branched chain C1 to C6 haloalkyl group such as fluoromethyl group, difluoromethyl group, trifluoromethyl group or the like; a carboxyl group; a straight chain or branched chain C1 to C6 alkoxycarbonyl group such as methoxycarbonyl group, ethoxycarbonyl group or the like; a halogen atom such as bromo group, chloro group, fluoro group, iodo group or the like; or a hydrogen atom.

Therefore, as the hydrazine compound represented by the general formula (2) usable in the step 1, there can be specifically mentioned, for example, phenylhydrazine, 2 methylphenylhydrazine, 4-methylphenylhydrazne, 2,4-dimethylphenylhydrazine, 2-ethylphenylhydrazine, 4 ethylphenylhydrazine, 4-isopropylphenylhydrazine, 2 methoxyphenylhydrazine, 4-methoxyphenylhydrazine, 2 methoxymethylphenylhydrazine, 4-methoxymethylphenylhydrazine, 4-trifluoromethylphenylhydrazine, 2-hydrazinobenzoic acid, 4-methoxycarbonylphenylhydrazine and 2-chlorophenylhydrazine.

The hydrazine compound represented by the general formula (2) can be any of a free form and a salt form (e.g. a hydrochloride or a sulfate).

The hydrazine compound represented by the general formula (2) is a known compound or a compound which can be produced from a corresponding raw material aniline according to, for example, the process described in Journal of Organic Chemistry, p. 2849 (1972).

Incidentally, of various hydrazine compounds represented by the general formula (2), 2-methoxymethylphenylhydrazine is a novel compound.

In the step 1 for producing a substituted indole compound represented by the general formula (3), the molar ratio of the hydrazine compound represented by the general formula (2)

and the (pyrimidine-2-yl)-2-propanone compound represented by the general formula (1) may be any level to allow the reaction between the two compounds to proceed. However, the (pyrimidine-2-yl)-2-propanone compound represented by the general formula (1) is used in an amount of, for example, ordinarily 0.5 to 3 moles, preferably 1 to 2 moles per mole of the hydrazine compound represented by the general formula (2).

The step 1 for producing the substituted indole compound represented by the general formula (3) is conducted using an acid. The acid usable can be exemplified by mineral acids such as hydrochloric acid, sulfuric acid and the like; acetic acids such as acetic acid, trifluoroacetic acid and the like; Lewis acids such as zinc chloride, boron trifluoride and the like: sulfonic acids such as p-toluenesulfonic acid and the like; phosphoric acids such as polyphosphoric acid and the like; phosphorus halides such as phosphorus trichloride and the like; and acidic ion exchange resins such as Amberlist and the like. Use of a Lewis acid such as zinc chloride, boron trifluoride or the like is preferred. The amount of the acid used in the step may be any amount as long as it does not decompose the formed substituted indole compound represented by the general formula (3); however, it may be 0.001 to 10 moles, preferably 0.1 to 2 moles per mole of the hydrazine compound represented by the general formula (2).

The step 1 for producing the substituted indole compound represented by the general formula (3) can allowed to proceed sufficiently even in a solvent-free state but can also be conducted using a solvent. The solvent used in the present reaction can be any solvent as long as it does not impair the reaction. There can be mentioned, for example, aromatic hydrocarbons such as toluene, xylene, chlorobenzene and the like; halogenated aliphatic hydrocarbons such as dichloromethane, chloroform and the like; acetic acid esters such as methyl acetate, ethyl acetate, butyl acetate and the like; aprotic polar solvents such as dimethylformamide, dimethylacetamide, N-methylpyrrolidone, tetramethylurea, hexamethylphosphoric triamide (HMPA) and the like; ether type solvents such as diethyl ether, tetrahydrofuran, dioxane and the like; and aliphatic hydrocarbons such as pentane, n-hexane and the like. Aromatic hydrocarbons such as toluene and the like are preferred. These solvents can be used singly or as a mixed solvent of any mixing ratio. The amount of the solvent may be any level as long as it can promise sufficient stirring of the reaction system, but it may be ordinarily 0.5 to 20 liters, preferably 1 to 10 liters per mole of the hydrazine compound represented by the general formula (2).

The reaction temperature used in the step 1 for producing the substituted indole compound represented by the general formula (3) is, for example, 0° C. to the reflux temperature of the solvent used, preferably 0° C. to 120° C.

There is no particular restriction as to the reaction time used in the step 1 for producing the substituted indole compound represented by the general formula (3), but the time is preferably 0.5 hour to 12 hours.

The substituted indole compound represented by the general formula (3), which can be produced in the step 1, is a novel compound and is useful as an intermediate for a sulfonanilide derivative known to have a high herbicidal activity and be useful.

The present invention process comprises a step (step 2) for oxidizing the indole ring of the above-obtained substituted indole compound represented by the general formula (3) to give rise to ring opening to produce a substituted acetanilide compound represented by the general formula (4) and steps for successively subjecting the acetanilide compound represented by the general formula (4) to reduction and deacetylation to produce a final product, i.e. a substituted aniline compound represented by the general formula (6). Any of the reduction and the deacetylation may be conducted first. Therefore, description is made, in the following order, on the above step 2, a step (step 3) for reacting the acetanilide compound represented by the general formula (4) with preferably sodium borohydride to produce a 2-(pyrimidine-2-ylhydroxymethyl)acetanilide compound represented by the general formula (5), and a step (step 4) for deacetylating the amide moiety of the 2-(pyrimidine-2-ylhydroxymethyl)acetanilide compound represented by the general formula (5), obtained in the step 3, to produce an final product, i.e. a substituted aniline compound represented by the general formula (6).

The step 2 is a step for oxidizing the substituted indole compound represented by the general formula (3), obtained in the step 1 to give rise to the ring opening of indole ring to produce a substituted acetanilide compound represented by the general formula (4). Incidentally, in the general formula (3), $R_1$, $R_2$, $R_3$, X and Y have the same definitions as given above.

The oxidizing agent used in the step 2 can be exemplified by ozone; inorganic peroxides such as hydrogen peroxide and the like; organic peroxides such as peracetic acid, perbenzoic acid, m-chloroperbenzoic acid and the like; metal oxides such as potassium permanganate, sodium periodate, sodium tungstate, ammonium molybdate and the like; and air. Ozone is preferred. These oxidizing agents can promise a sufficient reaction even when used singly, but can also be used in any mixing ratio. In the present oxidation step, the amount of the oxidizing agent used may be any level as long as it does not decompose the formed substituted acetanilide compound represented by the general formula (4), but the amount is ordinarily 0.1 to 20 moles, preferably 1 to 10 moles per mole of the substituted indole compound represented by the general formula (3).

In the step 2, the reaction is ordinarily conducted using a solvent. The solvent used may be any solvent as long as it does not impair the reaction. There can be mentioned, for example, acetic acid esters such as methyl acetate, ethyl acetate, butyl acetate and the like; halogenated aliphatic hydrocarbons such as dichloromethane, chloroform and the like; aromatic hydrocarbons such as toluene, xylene, chlorobenzene and the like; aliphatic hydrocarbons such as pentane, n-hexane and the like; aprotic polar solvents such as formamide, dimethylformamide, dimethylacetamide and the like; nitriles such as acetonitrile and the like; ether type solvents such as diethyl ether, tetrahydrofuran, dioxane, diglyme and the like; alcohols such as methanol, ethanol and the like; carboxylic acids such as acetic acid and the like; ketones such as acetone, methyl isobutyl ketone and the like; and water. The solvents may be used singly or as a mixed solvent of any mixing ratio. The amount of the solvent may be any level as long as it ensures sufficient stirring of the reaction system, but it is ordinarily 0.5 to 20 liters, preferably 1 to 10 liters per mole of the substituted indole compound represented by the general formula (3).

The reaction temperature of the step 2 may be, for example, −20° C. to the reflux temperature of the solvent used, but is preferably −10° C. to 60° C.

There is no particular restriction as to the reaction time of the step 2. However, the time is preferably 0.5 hour to 12 hours.

The substituted acetanilide compounds represented by the general formula (4), obtained in the step 2 are novel compounds and are useful as an intermediate for a sulfonanilide derivative known to be useful as a herbicide.

In this way, the substituted acetanilide compound represented by the general formula (4) can be produced.

As the acetanilide compound represented by the general formula (4), there can be specifically mentioned, for example, 2-(4,6-dimethoxypyrimidine-2-ylcarbonyl)acetanilide, 2-(4,6-dimethoxypyrimidine-2-ylcarbonyl)-6-methylacetanilide, 2-(4,6-dimethoxypyrimidine-2-ylcarbonyl)-6-ethylacetanilide, 2-(4,6-dimethoxypyrimidine-2-ylcarbonyl)-6-methoxymethylacetanilide, 2-(4,6-dimethoxypyrimidine-2-ylcarbonyl)-4-methylacetanilide, 2-(4,6-dimethoxypyrimidine-2-ylcarbonyl)-4-ethylacetanilide, 2-(4,6-dimethoxypyrimidine-2-ylcarbonyl)-4-methoxymethylacetanilide, 2-(4,6-dimethoxypyrimidine-2-ylcarbonyl)-4-chloroacetanilide, 2-(4,6-dimethoxypyrimidine-2-ylcarbonyl)-6-chloroacetanilide, 2-(4,6-dimethoxypyrimidine-2-ylcarbonyl)-4-fluoroacetanilide, and 2-(4,6-dimethoxypyrimidine-2-ylcarbonyl)-6-fluoroacetanilide.

The substituted acetanilide compound represented by the general formula (4), thus obtained in the step 2 can be used successively in the step 3 without being isolated or purified. That is, the substituted indole compound represented by the general formula (3) is subjected to the oxidation and ring-opening step of the step 2 with, for example, ozone and the like, and successively subjected to the reduction of the step 3 described later, with preferably sodium borohydride in the same vessel; thereby, a 2-(pyrimidine-2-ylhydroxymethyl)acetanilide compound represented by the general formula (5) can be obtained easily, and the post-treatment of the oxidizing agent used is also easy. Therefore, in view of the easiness of operation, etc., it is preferred industrially to employ a method of conducting such an oxidation and ring-opening step and such a reduction step continuously in the same vessel.

Next, description is made on the step 3.

The step 3 is a step for reducing the acetanilide compound represented by the general formula (4) with preferably sodium borohydride to produce a 2-(pyrimidine-2-ylhydroxymethyl)acetanilide compound represented by the general formula (5). Incidentally, in the general formula (4), $R_1$, $R_2$, $R_3$, X and Y have the same definitions as given above.

In the step 3, the molar ratio of the substituted acetanilide compound represented by the general formula (4) and sodium borohydride may be any level, but the amount of sodium borohydride may be 0.5 to 20 moles, preferably 1 to 10 moles per mole of the substituted acetanilide compound.

The reaction of the step 3 is conducted ordinarily using a solvent. The solvent used in the step 3 may be any solvent as long as it does not impair the reaction. There can be mentioned, for example, aromatic hydrocarbons such as toluene, xylene, chlorobenzene and the like; acetic acid esters such as methyl acetate, ethyl acetate, butyl acetate and the like; alcohols such as methanol, ethanol, 1-propanol, 2-propanol, 1-butanol and the like; aprotic polar solvents such as dimethylformamide, dimethylacetamide and the like; ether type solvents such as diethyl ether, tetrahydrofuran, dioxane and the like; aliphatic hydrocarbons such as pentane, n-hexane and the like; polyethylene glycols such as polyethylene glycol (PEG)-400 and the like; and water. The solvents can be used singly or as a mixed solvent of any mixing ratio. The amount of the solvent used may be any level as long as it ensures sufficient stirring of the reaction system, but is ordinarily 0.5 to 20 liters, preferably 1 to 10 liters per mole of the substituted acetanilide compound represented by the general formula (4):

The reaction temperature of the step 3 can be, for example, −15° C. to the reflux temperature of the solvent used, but is preferably −5° C. to 60° C.

There is no particular restriction as to the reaction time of the step 3, but it is preferably 0.5 hour to 24 hours.

Incidentally, in the step 3, it is preferred to use sodium borohydride for the stability of the reagent used as well as for a reason that the reagent is used also for the post-treatment of the oxidizing agent used in the step 2 for the oxidative ring-opening of substituted indole compound. However, the reduction in the step 3 is not restricted only to that by sodium borohydride and can also be, for example, a reduction by catalytic hydrogenation {as the catalyst, there can be used palladium carbon [Pd/C], platinum carbon [Pt/C], a Raney catalyst (e.g. Raney nickel), or a metallic catalytic reduction catalyst ordinary used}, a reduction by lithium aluminum hydride or a reduction by diborane.

The 2-(pyrimidine-2-ylhydroxymethyl)acetanilide compound represented by the general formula (5), obtained in the step 3 may be per se used in the next step 4 without being isolated.

Then, description is made on the step 4.

In the step 4, the 2-(pyrimidine-2-ylhydroxymethyl)acetanilide compound represented by the general formula (5), obtained in the step 3 is subjected to deacetylation at the amide moiety to produce an intended final compound, i.e. a substituted aniline compound represented by the general formula (6). Incidentally, in the general formula (5), $R_1$, $R_2$, $R_3$, X and Y have the same definitions as given above.

This deacetylation is preferably conducted using a base in view of the stability of the intended product.

As the base used in the reaction of the step 4, there can be mentioned, for example, alkali metal hydroxides such as sodium hydroxide, potassium hydroxide and the like; alkaline earth metal hydroxides such as barium hydroxide and the like; carbonates such as potassium carbonate, sodium carbonate and the like; and organic amines such as 1,8-diazabicyclo[5.4.0]undec-7-ene and the like. Of these, preferred are alkali metal hydroxides such as sodium hydroxide, potassium hydroxide and the like.

The amount of the base used in the step 4 may be any level as long as it does not decompose the formed substituted aniline compound represented by the general formula (6). However, the amount is ordinarily 0.1 to 30 moles, preferably 0.5 to 10 moles per mole of the 2-(pyrimidine-2-ylhydroxymethyl)acetanilide compound represented by the general formula (5).

The reaction of the step 4 may be conducted using a solvent. The solvent used in the step 4 is not critical as long as it does not impair the reaction. There can be mentioned, for example, aromatic hydrocarbons such as toluene, xylene, chlorobenzene and the like; alcohols such as methanol, ethanol and the like; aprotic polar solvents such as dimethylformamide, dimethylacetamide and the like; ether type solvents such as diethyl ether, tetrahydrofuran, dioxane and the like; aliphatic hydrocarbons such as pentane, n-hexane and the like; polyethylene glycols such as polyethylene glycol (PEG)-400 and the like; and water. The solvents may be used singly or as a mixed solvent of any mixing ratio. The amount of the solvent used may be any level as long as it ensures sufficient stirring of the reaction system, but it may be ordinarily 0.5 to 20 liters, preferably 1 to 10 liters per mole of the 2-(pyrimidine-2-ylhydroxymethyl)acetanilide compound represented by the general formula (5).

The reaction temperature of the step 4 can be, for example, −15° C. to the reflux temperature of the solvent used, but is preferably −5° C. to 100° C.

The reaction time of the step 4 is not critical but is preferably 0.5 hour to 24 hours.

As described previously, of the reduction and the deacetylation, of the acetanilide compound represented by the general formula (4), any may be conducted first. Therefore, there are described, in the following order, a step (step 5) for deacetylating the acetanilide compound represented by the general formula (4) to produce an amino compound represented by the general formula (7) and a step (step 6) for reducing the amino compound represented by the general formula (7) to produce a final product, i.e. a substituted aniline compound represented by the general formula (6).

The step 5 is a step for conducting solvolysis of the substituted acetanilide compound represented by the general formula (4), obtained in the step 2, using an acid to produce an amino compound represented by the general formula (7)

The acid used in the step 5 can be exemplified by mineral acids such as hydrochloric acid, sulfuric acid and the like; Lewis acids such as boron trifluoride and the like; acetic acids such as acetic acid, trifluoroacetic acid and the like; sulfonic acids such as p-toluenesulfonic acid and the like; and acidic ion exchange resins such as Amberlist and the like. Hydrochloric acid or sulfuric acid is used preferably.

The amount of the acid used in the step 5 can be any level as long as it does not decompose the formed amino compound represented by the general formula (7), but it is ordinarily 0.1 to 10 moles, preferably 0.5 to 5 moles per mole of the substituted acetanilide compound represented by the general formula (4).

The reaction of the step 5 is carried out in the presence of a solvent. The solvent Can be exemplified by water and straight chain or branched chain C1 to C6 alcohols such as ethanol, methanol and the like. The amount of the solvent may be 1 mole or more per mole of the substituted acetanilide compound represented by the general formula (4) and can be, for example, ordinarily 0.1 to 10 liters, preferably 0.5 to 10 liters per mole of the substituted acetanilide compound represented by the general formula (4). The amount differs depending upon the kind and amount of the acid used in the step 5, but may be such that the pH of the reaction system becomes approximately 4 or less, preferably 2 or less, more preferably 1 or less.

The reaction of the step 5 may be allowed to proceed sufficiently using the above solvent alone. However, the reaction may also be conducted by further adding other solvent.

The solvent usable by adding in the step 5 may be any solvent as long as it does not impair the solvolysis reaction of the step 5. There can be mentioned, for example, aromatic hydrocarbons such as toluene, xylene, chlorobenzene and the like; aprotic polar solvents such as dimethylformamide, dimethylacetamide and the like; ether type solvents such as diethyl ether, tetrahydrofuran, dioxane and the like; aliphatic hydrocarbons such as pentane, n-hexane and the like; nitriles such as acetonitrile and the like; and polyethylene glycols such as polyethylene glycol (PEG)-400 and the like. These solvents can be used in one kind or in admixture of two or more kinds.

When the reaction of the step 5 is conducted using an alcohol solvent, the alcohol used may react with the carbonyl group of an intended product and an acetal compound may be formed. In such a case, water is added in the presence of an acid or the reaction mixture is poured into water and stirring is made for several minutes to 48 hours, whereby acetal removal is made easily and an intended product can be obtained.

The amount of the solvent may be any level as long as it ensures sufficient stirring of the reaction system, but may be ordinarily 0.5 to 5 liters, preferably 1 to 3 liters per mole of the substituted acetanilide compound represented by the general formula (4).

The reaction temperature of the step 5 can be, for example, 0° C. to the reflux temperature of the solvent used and is preferably 0 to 120° C.

The reaction time of the step 5 is not critical but is preferably 0.5 hour to 24 hours.

The step 6 is a step for reducing the above-obtained amino compound represented by the general formula (7) with preferably sodium borohydride to produce a final product, i.e. a substituted aniline compound represented by the general formula (6). The outline and conditions of this reaction are about the same as in the step 3.

The thus-produced final product, i.e. the substituted aniline compound represented by the general formula (6) becomes an important intermediate in production of agricultural chemicals and medicines.

Meanwhile, the present invention also provides many novel compounds.

As described previously, of the hydrazine compounds represented by the general formula (2), 2-methoxymethylphenylhydrazine is a novel compound and can be produced from a corresponding raw material aniline according to, for example, the process described in Journal of Organic Chemistry, p. 2849 (1972).

Also, of the (pyrimidine-2-yl)-2-propanone compounds represented by the general formula (1), 1-(4,6-dimethoxypyrimidine-2-yl)-2-propanone is a novel compound and can be produced from a raw material such as 2-phenylsulfonyl-4,6-dimethoxypyrimidine or the like according to, for example, the process described in Chemical & Pharmaceutical Bulletin, p. 152 (1982). This compound has tautomers and all of the tautomers are included in the present invention.

Further, the substituted indole compound represented by the general formula (3) is a novel compound and can be produced by the step 1. Incidentally, in the general formula (4), $R_1$, $R_2$, $R_3$, X and Y have the same definitions as given above.

In the following Table 1, examples of the substituted indole compound represented by the general formula (3) are shown. However, the present invention compound is not restricted to these and includes all of the compounds represented by the general formula (3).

Incidentally, the symbols shown in Table 1 have the following meanings (the same applies to the following tables).

Me: methyl group

Et: ethyl group

MOM: methoxymethyl group

MeO: methoxy group

EtO: ethoxy group i-Pr: isopropyl group

COOMe: methoxycarbonyl group $NO_2$: nitro group $CF_3$: trifluoromethyl group

NHAc: acetamide group

TABLE 1

| Compound No. | X | Y | R₁ | R₂ | R₃ | Melting point (° C.) |
|---|---|---|---|---|---|---|
| 3-1 | H | H | OMe | H | OMe | 182-184 |
| 3-2 | Me | H | Me | H | Me | |
| 3-3 | H | Me | OMe | H | OMe | 145-147 |
| 3-4 | H | Et | H | H | H | |
| 3-5 | Me | Me | OMe | NO₂ | OMe | |
| 3-6 | H | MeO | OMe | Me | OMe | |
| 3-7 | EtO | H | OMe | COOMe | OMe | |
| 3-8 | H | MOM | OMe | H | OMe | 176-189 |
| 3-9 | Cl | H | OEt | H | OEt | |
| 3-10 | H | F | H | NHAc | H | |
| 3-11 | H | COOH | Cl | H | Cl | |
| 3-12 | COOMe | H | H | MOM | H | |
| 3-13 | Me | COOMe | H | CF₃ | H | |
| 3-14 | Cl | Me | OMe | H | OMe | |
| 3-15 | i-Pr | H | OMe | H | OMe | |
| 3-16 | Cl | Me | OMe | H | OMe | 179-181 |
| 3-17 | i-Pr | H | OMe | H | OMe | 156-158 |
| 3-18 | H | Et | OMe | H | OMe | 90-95 |

Further, the substituted acetanilide compound represented by the general formula (4) is also a novel compound and can be produced by the step 2. Incidentally, in the general formula (3), $R_1, R_2, R_3, X, Y$ and Ac have the same definitions as given above.

In the following Table 2, examples of the substituted acetanilide compound represented by the general formula (4) are shown. However, the present invention compound is not restricted to these and includes all of the compounds represented by the general formula (4).

TABLE 2

| Compound No. | X | Y | R₁ | R₂ | R₃ | Melting point (° C.) |
|---|---|---|---|---|---|---|
| 4-1 | H | H | OMe | H | OMe | |
| 4-2 | Me | H | Me | H | Me | |
| 4-3 | H | Me | OMe | H | OMe | 151-153 |
| 4-4 | H | Et | H | H | H | |
| 4-5 | Me | Me | OMe | NO₂ | OMe | |
| 4-6 | H | MeO | OMe | Me | OMe | |
| 4-7 | EtO | H | OMe | COOMe | OMe | |
| 4-8 | H | MOM | OMe | H | OMe | 147-150 |
| 4-9 | Cl | H | OEt | H | OEt | |
| 4-10 | H | F | H | NHAc | H | |
| 4-11 | H | COOH | Cl | H | Cl | |
| 4-12 | COOMe | H | H | MOM | H | |
| 4-13 | Me | COOMe | H | CF₃ | H | |
| 4-14 | Cl | Me | OMe | H | OMe | |
| 4-15 | i-Pr | H | OMe | H | OMe | |
| 4-16 | Cl | H | OMe | H | OMe | 142-144 |
| 4-17 | OMe | H | OMe | H | OMe | 136-137 |
| 4-18 | H | Et | OMe | H | OMe | 139-142 |

Furthermore, the 2-(pyrimidine-2-ylhydroxymethyl)acetanilide compound represented by the general formula (5) is also a novel compound and can be produced by the step 3 [or directly from the substituted indole compound represented by the general formula (3) without via the substituted acetanilide compound represented by the general formula (4)]. Incidentally, in the general formula (5), $R_1, R_2, R_3, X, Y$ and Ac have the same definitions as given above.

In the following Table 3, examples of the 2-(pyrimidine-2-ylhydroxymethyl)acetanilide compound represented by the general formula (5) are shown. However, the present invention compound is not restricted to these and includes all of the compounds represented by the general formula (5).

TABLE 3

| Compound No. | X | Y | R₁ | R₂ | R₃ | Melting point (° C.) |
|---|---|---|---|---|---|---|
| 5-1 | H | H | OMe | H | OMe | |
| 5-2 | Me | H | Me | H | Me | |
| 5-3 | H | Me | OMe | H | OMe | |
| 5-4 | H | Et | OMe | H | OMe | 143-147 |
| 5-5 | Me | Me | OMe | NO₂ | OMe | |
| 5-6 | H | MeO | OMe | Me | OMe | |
| 5-7 | EtO | H | OMe | COOMe | OMe | |
| 5-8 | H | MOM | OMe | H | OMe | 79-82 |
| 5-9 | Cl | H | OEt | H | OEt | |
| 5-10 | H | F | H | NHAc | H | |
| 5-11 | H | COOH | Cl | H | Cl | |
| 5-12 | COOMe | H | H | MOM | H | |
| 5-13 | Me | COOMe | H | CF₃ | H | |
| 5-14 | Cl | Me | OMe | H | OMe | |
| 5-15 | i-Pr | H | OMe | H | OMe | |
| 5-16 | Cl | H | OMe | H | OMe | 121-123 |
| 5-17 | OMe | H | OMe | H | OMe | 122-125 |

There is shown below an example of the reaction scheme for obtaining a sulfonanilide compound (which can become a herbicide) from a substituted aniline compound represented by the general formula (6) which is obtained from a compound represented by the general formula (1) via various general formula compounds.

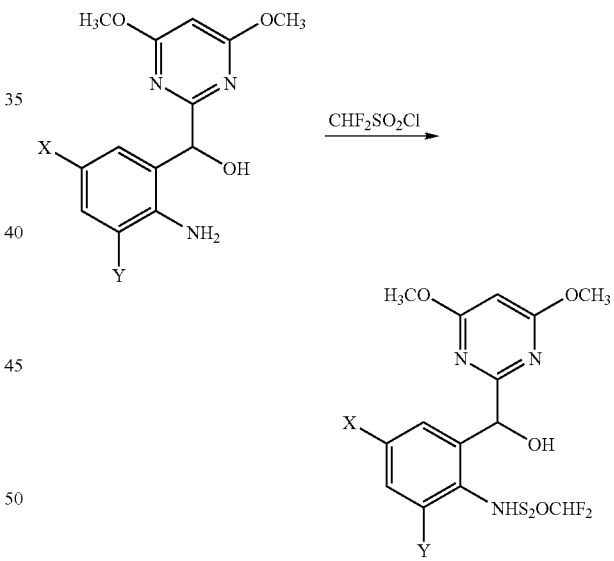

As shown in the above reaction scheme, the present invention process and the present invention compound are very useful in production of a sulfonanilide compound which is useful as an effective ingredient of herbicide.

Then, the process for production of the present invention compound is described specifically by way of Examples. In the Examples, refractive index $n^{20}_D$ indicates a refractive index measured at 20° C. using a sodium D line. Gas chromatography was conducted using, as a column, G-250 (40 m) [a product of (Zai) Kagaku Busshitsu Hyoka Kenkyu Kiko (formerly, Kagakuhin Kensa Kyokai). High-performance liquid chromatography was conducted using, as a column, YMC-A312 (a product of K.K. YMC and, as a elutant, an aqueous acetonitrile/0.05% phosphoric acid solution.

Example 1

Production of 2-methoxymethylphenylhydrazine 6.86 g (50 m moles) of 2-methoxymethylaniline was dissolved in 50 ml of concentrated hydrochloric acid. The solution was cooled to −10° C. Thereto was dropwise added a solution of sodium nitrite (4.14 g, 60 m moles) dissolved in water (50 ml) while a temperature of −10° C. to 0° C. was being kept. Then, a solution of 44.6 g (235 m moles) of stannous chloride dissolved in concentrated hydrochloric acid (50 ml) was dropwise added at the above temperature in 1 hour. After the completion of the dropwise addition, stirring was conducted with a gradual temperature increase to about 20° C. Then, a 10% aqueous sodium hydroxide solution was dropped to obtain a pH of 14, after which extraction with toluene was conducted. The toluene layer was washed with water and concentrated under reduced pressure using a rotary evaporator to obtain 5.40 g (35.5 m moles) of liquid 2-methoxymethylphenylhydrazine. Yield: 710.

MS m/e: 152 (W)
$^1$H-NMR (CDCl$_3$/TMS), δ (ppm):
3.8 (s, 3H), 4.46 (s, 2H), 7.1 to 7.4 (m, 7H)
IR (NaCl plate, cm$^{-1}$): 3350 (NH)

Example 2

Production of 1-(4,6-dimethoxypyrimidine-2-yl)-2-propanone

In a reactor were placed 16.0 g (0.4 moles) of 60% sodium hydride, 400 ml of THF and 43.6 g (0.2 moles) of 4,6-dimethoxy-2-methanesulfonylpyrimidine. The reactor contents were heated to 30° C. Thereto was dropwise added 39.4 g (0.68 moles) of acetone, followed by a reaction for 2 hours. After the completion of the reaction, 350 ml of water was added and extraction with 500 ml of ethyl acetate was conducted. The ethyl acetate layer was concentrated. The concentrate was subjected to distillation under reduced pressure to obtain 8.8 g (44.9 m moles) of 1-(4,6-dimethoxypyrimidine-2-yl)-2-propanone. Refractive index $n^{20}_D$: 1.5181

MS m/e: 196 (M$^+$)
$^1$H-NMR (CDCl$_3$/TMS), δ (ppm):
2.03 (s), 2.26 (s), 3.86 (s), 3.91 (s, 6H), 5.40 (s), 5.73 (s), 5.91 (s, 1H)

Example 3

Step 1

Production of 3-(4,6-dimethoxypyrimidine-2-yl)-2-methyl-7-ethylindole

Into a reactor were fed 2.4 g (12.2 m moles) of 1-(4,6-dimethoxypyrimidine-2-yl)-2-propanone, 1.7 g (9.98 m moles) of 2-ethylphenylhydrazine hydrochloride, 1.4 g (10.2 m moles) of zinc chloride and 10 ml of toluene, followed by refluxing for 2 hours with heating. After the completion of the reaction, the reaction mixture was cooled to room temperature. Thereto were added water and ethyl acetate and phase separation was made. The ethyl acetate layer was concentrated. The concentrate was subjected to silica gel column chromatography separation (developing solvent: n-hexane/ethyl acetate) to obtain 2.38 g (8.01 m moles) of 3-(4,6-dimethoxypyrimidine-2-yl)-2-methyl-7-ethylindole.

Yield: 80.3% Melting point: 90.3 to 94.8° C.
MS m/e: 297 (M$^+$)
$^1$H-NMR (CDCl$_3$/TMS), δ (ppm):
1.38 (t, 3H), 2.87 (q, 2H), 2.96 (s, 3H), 4.08 (s, 6H), 5.85 (s, 1H), 7.03 (d, 1H), 7.18 (t, 1H), 8.18 (bs, 1H), 8.57 (d, 1H)

Example 4

Step 2

Production of 2-(4,6-dimethoxypyrimidine-2-ylcarbonyl)-6-ethylacetanilide

Into a reactor were fed 0.7 g (2.4 m moles) of 3-(4,6-dimethoxypyrimidine-2-yl)-2-methyl-7-ethylindole and 10 ml of ethyl acetate. Then, ozone was blown into at 0° C. to 10° C. for 2 hours. After the completion of the reaction, the reaction mixture was heated to room temperature and concentrated. As a result, 0.75 g (2.3 m moles) of 2-(4,6-dimethoxypyrimidine-2-ylcarbonyl)-6-ethylacetanilide was formed. Yield: 95%.

Melting point: 139.3 to 142.3° C.
MS m/e: 329 (M$^+$)
$^1$H-NMR (CDCl$_3$/TMS), δ (ppm):
1.25 (t, 3H), 2.17 (s, 3H), 2.69 (q, 2H), 3.95 (s, 6H), 6.16 (s, 1H), 7.2 to 7.3 (m, 1H), 7.4 to 7.6 (m, 2H), 8.95 (bs, 1H)

Example 5

Step 3

Production of 2-(4,6-dimethoxypyrimidine-2-ylhydroxymethyl)-6-ethylacetanilide In a reactor were placed 1.0 g (3.03 m moles) of 2-(4,6-dimethoxypyrimidine-2-ylcarbonyl)-6-ethylacetanilide and 20 ml of ethanol. The reactor contents were cooled to 5° C. or less. Then, 0.13 g (3.65 m moles) of sodium borohydride was added, and stirring was made at the same temperature for 1 hour. Then, the reaction mixture was heated to room temperature. After the completion of the reaction, an aqueous ammonium chloride solution was added and extraction with ethyl acetate was made. The organic layer was concentrated to obtain 0.82 g (2.48 m moles) of 2-(4,6-dimethoxypyrimidine-2-ylhydroxymethyl)-6-ethylacetanilide.

Yield: 82% Melting point: 143 to 147° C.
MS m/e: 331 (le)
$^1$H-NMR (CDCl$_3$/TMS), δ (ppm):
1.24 (t, 3H), 2.22 (s, 3H), 2.64 (q, 2H), 3.97 (s, 6H), 4.88 (d, 1H), 5.89 (d, 1H), 5.95 (s, 1H), 7.2 to 7.5 (m, 3H), 9.25 (bs, 1H)

Example 6

Step 4

Production of 2-(4,6-dimethoxypyrimidine-2-ylhydroxymethyl)-6-ethylaniline

In a reactor were placed 0.1 g (0.30 m moles) of 2-(4,6-dimethoxypyrimidine-2-ylhydroxymethyl)-6-ethylacetanilide, 2 ml of methanol and 2 ml of water. Then, 60 mg (1.1 m moles) of potassium hydroxide was added. Stirring was conducted at 70° C. for 6 hours. After the completion of the reaction, high-performance liquid column chromatography was conducted. As a result, 2-(4,6-dimethoxypyrimidine-2-ylhydroxymethyl)-6-ethylaniline was formed by 65%.

Example 7

Step 1

Production of 3-(4,6-dimethoxypyrimidine-2-yl)-2-methyl-7-methoxymethylindole Into a reactor were fed 6.2 g (31.6 m moles) of 1-(4,6-dimethoxypyrimidine-2-yl)-2-propanone, 4.8 g (31.5 m moles) of 2-methoxymethylphenylhydrazine, 4.76 g (34.9 m moles) of zinc chloride and 60 ml of toluene. Refluxing was made for 2 hours with heating. After the completion of the reaction, the reaction mixture was cooled to room temperature. Water and ethyl acetate were added and phase separation was made. The ethyl acetate layer was concentrated. The resulting crystals were washed with diisopropyl ether to obtain 4.57 g (14.6 m moles) of 3-(4,6-dimethoxypyrimidine-2-yl)-2-methyl-7-metoxymethylindole. Yield: 46%, MS m/e: 313 ($M^+$)

$^1$H-NMR (CDCl$_3$/TMS), δ (ppm):

2.95 (s, 3H), 3.34 (s, 3H), 4.06 (s, 6H), 4.74 (s, 2H), 5.81 (s, 1H), 7.0 to 7.1 (m, 3H), 8.65 (d, 1H)

The obtained 3-(4,6-dimethoxypyrimidine-2-yl)-2-methyl-7-methoxymethylindole can be used in the reaction of step 2 based on Example 4.

Example 8

Step 2

Production of 2-(4,6-dimethoxypyrimidine-2-ylcarbonyl)-6-methoxymethylacetanilide In a reactor were placed 1.0 g (31.9 m moles) of 3-(4,6-dimethoxypyrimidine-2-yl)-2-methyl-7-methoxymethylindole and 40 ml of ethyl acetate. Thereinto was blown ozone at 0° C. to 10° C. for 4 hours. After the completion of the reaction, the reactor contents were heated to room temperature and concentrated. The residue was subjected to silica gel column chromatography separation (developing solvent: n-hexane/ethyl acetate) to obtain 0.40 g (11.6 m moles) of 2-(4,6-dimethoxypyrimidine-2-ylcarbonyl)-6-methoxymethylacetanilide. Melting point 147 to 150° C. Yield: 36.4%

MS m/e: 345 ($M^+$)

$^1$H-NMR (CDCl$_3$/TMS), δ (ppm):

2.13 (s, 3H), 3.39 (s, 3H), 3.94 (s, 6H), 4.47 (s, 2H), 6.15 (s, 1H), 7.26 (t, 1H), 7.60 (d, 2H), 7.63 (d, 1H), 9.29 (b, 1H)

The obtained 2-(4,6-dimethoxypyrimidine-2-ylcarbonyl)-6-methoxymethylacetanilide could be used in the reaction of step 3 according to Example 5.

Example 9

Continuous Operation of Step 3 and Step 4 in One Same Reactor

Production of 2-(4,6-dimethoxypyrimidine-2-ylcarbonyl)-6-methoxymethylaniline In a reactor were placed 1.0 g (2.9 m moles) of 2-(4,6-dimethoxypyrimidine-2-ylcarbonyl)-6-methoxymethylacetanilide and 20 ml of ethanol, followed by cooling to 5° C. or less. Therein was placed 0.5 g (13.5 m moles) of sodium borohydride. Stirring was conducted at the same temperature for 1 hour. Then, the mixture was heated to room temperature. After the completion of the reaction, an aqueous ammonium chloride solution was added and extraction with ethyl acetate was made. The organic layer was concentrated. To the residue were added 20 ml of water and 0.4 g (7.1 m moles) of potassium hydroxide, followed by stirring at 70° C. for 2 hours. After the completion of the reaction, the reaction mixture was cooled to room temperature, and there were added 50 ml of ethyl acetate and 50 ml of water to conduct extraction. The organic layer was concentrated and the concentrate was subjected to silica gel column chromatography separation (developing solvent: n-hexane/ethyl acetate) to obtain 0.35 g (1.48 m moles) of 2-(4,6-dimethoxypyrimidine-2-ylhydroxymethyl)-6-methoxymethylaniline. Yield: 51.0%

Example 10

Step 1

Production of 3-(4,6-dimethoxypyrimidine-2-yl)-2-methylindole

In 10 ml of toluene were dissolved 1.61 g (8.2 m moles) of 1-(4,6-dimethoxypyrimidine-2-yl)-2-propanone and 1.08 g (10 m moles) of phenylhydrazine. Thereto was added 1.36 g (10 m moles) of zinc chloride, followed by refluxing for 1 hour. The reaction mixture was allowed to cool, and ethyl acetate and water were added to dissolve the whole reaction mixture. The oily layer was washed with water, separated and dried over Glauber's salt. The resulting oily layer was concentrated under reduced pressure to obtain an orange solid. The solid was recrystallized from methanol to obtain 1.37 g (5.1 m moles) of 3-(4,6-dimethoxypyrimidine-2-yl)-2-methylindole. Yield: 62% Melting point: 182 to 184° C.

MS m/e: 269 (le)

$^1$H-NMR (CDCl$_3$/TMS), δ (ppm):

2.94 (s, 3H), 4.06 (s, 6H), 5.81 (s, 1H), 7.1 (m, 2H), 7.3 (m, 1H), 8.7 (m, 1H)

IR (KBr, cm$^{-1}$): 3490 (NH), 1570

The obtained 3-(4,6-dimethoxypyrimidine-2-yl)-2-methylindole could be used in the reaction of step 2 according to Example 4 or Example 8.

Example 11

Step 2

Production of 2-(4,6-dimethoxypyrimidine-2-ylcarbonyl)acetanilide

In a reactor were fed 0.8 g (3.0 m moles) of 3-(4,6-dimethoxypyrimidine-2-yl)-2-methylindole, 30 ml of acetone and 8 ml of water. Then, there were added 1.5 g (9.9 m moles) of potassium permanganate and 2.29 g (10.7 m moles) of sodium periodate, and a reaction was allowed to take place at room temperature for 12 hours. After the completion of the reaction, filtration was made. The filtrate was subjected to extraction with ethyl acetate. The ethyl acetate layer was concentrated. The residue was washed with isopropyl ether to obtain 0.57 g (1.9 m moles) of 2-(4,6-dimethoxypyrimidine-2-ylcarbonyl)acetanilide. Yield: 63%

MS m/e: 301 ($M^+$)

$^1$H-NMR (CDCl$_3$/TMS), δ (ppm):

2.28 (s, 3H), 3.96 (s, 6H), 6.16 (s, 1H), 7.06 (t, 1H) 7.27 (b, 1H), 7.59 (d, 1H), 8.78 (d, 1H)

IR (KBr, cm$^{-1}$): 3270 (NH), 1700, 1660 (C=O)

The obtained 2-(4,6-dimethoxypyrimidine-2-ylcarbonyl) acetanilide could be used in the reaction of step 3 according to Example 5 or Example 9.

Example 12

Step 1

Production of 3-(4,6-dimethoxypyrimidine-2-yl)-2,7-dimethylindole

In 20 ml of toluene were dissolved 0.77 g (3.9 m moles) of 1-(4,6-dimethoxypyrimidine-2-yl)-2-propanone and 0.69 g (4.3 m moles) of 2-methylphenylhydrazine hydrochloride. Thereto was added 0.64 g (4.7 m moles) of zinc chloride, followed by refluxing for 2 hours. The reaction mixture was allowed to cool, and then ethyl acetate and water were added to dissolve the whole reaction mixture. The oily layer was washed with water, separated and dried over Glauber's salt. The resulting oily layer was concentrated under reduced pressure using a rotary evaporator, to obtain an orange solid. The solid was treated with ethyl acetate/n-hexane to obtain 0.38 g (1.34 m moles) of 3-(4,6-dimethoxypyrimidine-2-yl)-2,7-dimethylindole. Yield: 34% Melting point: 145 to 147° C.

MS m/e: 283 (W)

$^1$H-NMR (CDCl$_3$/TMS), δ (ppm):

2.47 (s, 3H), 2.90 (s, 3H), 4.05 (s, 6H), 5.83 (s, 1H), 6.98 (d, 1H), 7.13 (t, 1H), 8.15 (d, 1H), 8.50 (d, 1H)

IR (cm$^{-1}$): 3350 (NH)

The obtained 3-(4,6-dimethoxypyrimidine-2-yl)-2,7-dimethylindole could be used in the reaction of step 2 according to Example 4 or Example 8 or Example 12.

Example 13

Step 2

Production of 2-(4,6-dimethoxypyrimidine-2-ylcarbonyl)acetanilide

In a reactor were placed 1.0 g (3.7 m moles) of 3-(4,6-dimethoxypyrimidine-2-yl)-2-methylindole, 30 ml of acetone and 15 ml of water. Thereto was added 3.0 g (19 m moles) of potassium permanganate and a reaction was allowed to take place at room temperature for 12 hours. After the completion of the reaction, the reaction mixture was subjected to gas chromatography. As a result, 2-(4,6-dimethoxypyrimidine-2-ylcarbonyl)acetanilide was formed by 74% in terms of total area ratio.

Example 14

Step 2

Production of 2-(4,6-dimethoxypyrimidine-2-ylcarbonyl)-6-methylacetanilide

In a reactor were placed 283 mg (1.0 m moles) of 3-(4,6-dimethoxypyrimidine-2-yl)-2,7-dimethylindole and 15 ml of acetone. Thereto were added 790 mg (5.0 m moles) of potassium permanganate and 214 mg (1.0 m moles) of sodium periodate, and a reaction was allowed to take place for 12 hours. After the completion of the reaction, the reaction mixture was filtered. The filtrate was extracted with ethyl acetate. The ethyl acetate layer was concentrated. The residue was washed with isopropyl ether to obtain 80 mg (0.25 m moles) of 2-(4,6-dimethoxypyrimidine-2-ylcarbonyl)-6-methylacetanilide. Yield: 25% Melting point: 151 to 153° C.

MS m/e: 315 (M$^+$)

$^1$H-NMR (CDCl$_3$/TMS), δ (ppm):

2.47 (s, 3H), 2.90 (s, 3H), 4.05 (s, 6H), 5.83 (s, 1H), 6.98 (d, 1H), 7.13 (t, 1H), 8.15 (b, 1H), 8.50 (d, 1H)

The obtained 2-(4,6-dimethoxypyrimidine-2-ylcarbonyl)-6-methylacetanilide could be used in the reaction of step 3 according to Example 5 or Example 9.

Example 15

Step 2

Production of 2-(4,6-dimethoxypyrimidine-2-ylcarbonyl)acetanilide

In a reactor were placed 0.27 g (10 m moles) of 3-(4,6-dimethoxypyrimidine-2-yl)-2-methylindole and 10 ml of ethyl acetate. Then, ozone was blown into at 0° C. to 10° C. for 3 hours. After the completion of the reaction, the reaction mixture was heated to room temperature and concentrated. The residue was subjected to gas chromatography. As a result, 2-(4,6-dimethoxypyrimidine-2-ylcarbonyl)acetanilide was formed by 88% in terms of total area ratio.

Example 16

Step 2

Production of 2-(4,6-dimethoxypyrimidine-2-ylcarbonyl)-6-methylacetanilide

In a reactor were placed 3-(4,6-dimethoxypyrimidine-2-yl)-2,7-dimethylindole and ethyl acetate. Then, ozone was blown thereinto at 0° C. to 10° C. for 3 hours. After the completion of the reaction, the reaction mixture was heated to room temperature and concentrated. The residue was subjected to gas chromatography. As a result, 2-(4,6-dimethoxypyrimidine-2-ylcarbonyl)-6-methylacetanilide was formed by 63% in terms of total area ratio.

Example 17

Step 2

Production of 2-(4,6-dimethoxypyrimidine-2-ylcarbonyl)-6-ethylacetanilide

In a reactor were placed 0.5 g (1.7 m moles) of 3-(4,6-dimethoxypyrimidine-2-yl)-2-methyl-7-ethylindole, 10 ml of acetone and 5 ml of water. Thereto were added potassium permanganate and sodium periodate, and stirring was made at room temperature to give rise to a reaction. The reaction mixture was subjected to gas chromatography. As a result, 2-(4,6-dimethoxypyrimidine-2-ylcarbonyl)-6-ethylacetanilide was formed by 47% in terms of total area ratio.

Example 18

Step 3

Production of 2-(4,6-dimethoxypyrimidine-2-ylhydroxymethyl)-6-methoxymethylacetanilide In a reactor were placed 1.7 g (4.9 m moles) of 2-(4,6-dimethoxypyrimidine-2-ylcarbonyl)-6-methoxymethylacetanilide and 20 ml of ethanol. The reactor contents were cooled to 5° C. or less. Thereto was added 0.4 g (10.8 m moles) of sodium borohydride, and the mixture was stirred at the same temperature for 1 hour to give rise to a reaction. Then, the mixture was heated to room temperature. After the completion of the reaction, an aqueous ammonium chloride solution was added and extraction with ethyl acetate was made. The organic layer was concentrated to obtain 1.32 g (3.8 m moles) of 2-(4,6-dimethoxypyrimidine-2-ylhydroxymethyl)-6-methoxymethylacetanilide. Yield: 78%

Melting point: 79 to 82° C.
MS m/e: 347 (M$^+$)
$^1$H-NMR (CDCl$_3$/TMS), δ (ppm):
2.24 (s, 3H, 3.38 (s, 3H), 3.97 (s, 6H), 4.45 (q, 2H), 4.87 (d, 1H), 5.90 (d, 1H), 7.2 to 7.3 (m, 1H), 7.46 (d, 2H), 9.41 (bs, 1H)

The obtained 2-(4,6-dimethoxypyrimidine-2-ylhydroxymethyl)-6-methoxymethylacetanilide could be used in the reaction of step 4 according to Example 6.

Example 19

Continuous Operation of Step 2 and Step 3 in One Same Reactor

Production of 2-(4,6-dimethoxypyrimidine-2-ylhydroxymethyl)-6-ethylacetanilide

In a reactor were placed 1.0 g (3.37 m moles) of 3-(4,6-dimethoxypyrimidine-2-yl)-2-methyl-7-ethylindole and 20 ml of ethyl acetate. The reactor contents were cooled to 5° C. or less. Then, ozone was blown into at 0° C. to 10° C. for 2 hours. After the completion of the reaction, 20 ml of ethanol was added. Further, 0.25 g (6.76 m moles) of sodium borohydride was added and stirring was conducted for 1 hour. After the completion of the reaction, the reaction mixture was heated to room temperature. An aqueous ammonium chloride solution and ethyl acetate were added to conduct extraction. The organic layer was concentrated and the concentrate was subjected to silica gel column chromatography separation (developing solvent: n-hexane/ethyl acetate) to obtain 0.26 g (0.79 m moles) of 2-(4,6-dimethoxypyrimidine-2-ylhydroxymethyl)-6-ethylacetanilide. Yield: 27.4%

The obtained 2-(4,6-dimethoxypyrimidine-2-ylhydroxymethyl)-6-ethylacetanilide could be used in the reaction of step 4 according to Example 6.

Example 20

Continuous Operation of Step 3 and Step 4 in One Same Reactor

Production of 2-(4,6-dimethoxypyrimidine-2-ylhydroxymethyl)-6-methoxymethylaniline In a reactor were placed 1.0 g (2.9 m moles) of 2-(4,6-dimethoxypyrimidine-2-ylcarbonyl)-6-methoxymethylacetanilide produced in accordance with Example 8 and 20 ml of ethanol. The reactor contents were cooled to 5° C. or less. Thereto was added 0.5 g (13.5 m moles) of sodium borohydride, followed by stirring at the same temperature for 1 hour. Then, the mixture was heated to room temperature. After the completion of the reaction, an aqueous ammonium chloride solution was added and extraction was made with ethyl acetate. The organic layer was concentrated. To the residue were added 20 ml of methanol and 1.5 g (26.8 m moles) of potassium hydroxide. The mixture was stirred at 70° C. for 2 hours. After the completion of the reaction, the reaction mixture was cooled to room temperature, and 50 ml of ethyl acetate and 50 ml of water were added to conduct extraction. The organic layer was concentrated. The concentrate was subjected to silica gel column chromatography separation (developing solvent: n-hexane/ethyl acetate) to obtain 0.24 g (0.79 m moles) of 2-(4,6-dimethoxypyrimidine-2-ylhydroxymethyl)-6-methoxymethylaniline. Yield: 27.10

$^1$H-NMR (CDCl$_3$/TMS), δ (ppm):
3.31 (s, 3H), 3.94 (s, 6H), 4.51 (dd, 2H), 4.66 (bs, 1H), 5.15 (bs, 2H), 5.84 (s, 1H), 5.93 (s, 1H), 6.71 (t, 1H), 6.7 to 6.8 (m, 1H), 6.9 to 7.1 (m, 1H), 7.2 to 7.3 (m, 1H)

Example 21

Continuous Operation of Step 2 and Step 3 in One Same Reactor

Production of 2-(4,6-dimethoxypyrimidine-2-ylhydroxymethyl)-6-methoxymethylacetanilide In a reactor were placed 1.0 g (3.19 m moles) of 3-(4,6-dimethoxypyrimidine-2-yl)-2-methyl-7-methoxymethylindole and 20 ml of ethyl acetate. The reactor contents were cooled to 5° C. or less. Then, ozone was blown into at 0° C. to 10° C. for 3 hours. (after the completion of the reaction, 20 ml of ethanol was added. Further, 0.5 g (13.5 m moles) of sodium borohydride was added, followed by stirring for 1 hour. After the completion of the reaction, the reaction mixture was heated to room temperature, and an aqueous ammonium chloride solution and ethyl acetate were added to conduct extraction. The organic layer was concentrated. The concentrate was subjected to column chromatography separation to obtain 0.18 g (0.52 m moles) of 2-(4,6-dimethoxypyrimidine-2-ylhydroxymethyl)-6-methoxymethylacetanilide. Yield: 16.3%

The obtained 2-(4,6-dimethoxypyrimidine-2-ylhydroxymethyl)-6-methoxymethylacetanilide could be used in the reaction of step 4 in accordance with Example 6.

Example 22

Step 5

Production of 2-(4,6-dimethoxypyrimidine-2-ylcarbonyl)aniline

In a reactor were placed 0.57 g (1.9 m moles) of 2-(4,6-dimethoxypyrimidine-2-ylcarbonyl)acetanilide, 10 ml of methanol and 5 ml of 6 N hydrochloric acid, followed by refluxing for 1 hour with heating. After the completion of the reaction, the reaction mixture was made alkaline with sodium hydroxide, after which extraction with ethyl acetate was made. The ethyl acetate layer was concentrated. The residue was subjected to gas chromatography. As a result, formation of 2-(4,6-dimethoxypyrimidine-2-ylcarbonyl)aniline was confirmed. Conversion: 1000 (in terms of total area ratio in gas chromatography)

Example 23

Step 5

Production of 2-(4,6-dimethoxypyrimidine-2-ylcarbonyl)-6-methoxymethylaniline 50 ml of methanol and 10 ml of concentrated sulfuric acid were mixed in a reactor. Thereto was added 1.0 g (2.9 m moles) of 2-(4,6-dimethoxypyrimidine-2-ylcarbonyl)-6-methoxymethylacetanilide, followed by refluxing at 65° C. for 4 hours. Then, the reaction mixture was allowed to cool to room temperature. 50 ml of water was added and stirring was conducted at about 20° C. overnight. After the completion of the reaction, the reaction mixture was poured into water and extraction with ethyl acetate was made. The ethyl acetate layer was concentrated. The residue was subjected to column chromatography separation to obtain 0.30 g (1 m moles) of 2-(4,6-dimethoxypyrimidine-2-ylcarbonyl)-6-methoxymethylaniline.

Yield: 34%

Example 24

Continuous Operation of Step 2 and Step 5 in One Same Reactor

Production of 2-(4,6-dimethoxypyrimidine-2-ylcarbonyl)aniline

In a reactor were placed 0.60 g (22 m moles) of 3-(4,6-dimethoxypyrimidine-2-yl)-2-methylindole and 20 ml of ethyl acetate. Thereinto was blown ozone at 0° C. to 10° C. for 4 hours. Thin-layer chromatography was conducted to confirm the disappearance of 3-(4,6-dimethoxypyrimidine-2-yl)-2-methylindole and complete a reaction. Then, the reaction mixture was heated to room temperature and concentrated. To the concentrate were added 20 ml of methanol and 5 ml of 6 N hydrochloric acid, and refluxing was made for 1 hour with heating. After the completion of the reaction, the reaction mixture was cooled to room temperature. 100 ml of water was added. The mixture was made alkaline with an aqueous sodium hydroxide solution, and extraction was made with ethyl acetate. The organic layer was concentrated. The concentrate was subjected to column chromatography separation to obtain 0.26 g (10 m moles) of 2-(4,6-dimethoxypyrimidine-2-ylcarbonyl)aniline. Yield: 46%

MS m/e: 259 (W)

$^1$H-NMR (CDCl$_3$/TMS), δ (ppm):

3.99 (s, 6H), 6.18 (s, 1H), 6.42 (b, 2H), 6.5 to 6.6 (m, 1H), 6.70 (d, 1H), 7.2 to 7.3 (m, 1H), 7.40 (d, 1H)

Example 25

Step 1

Production of 5-chloro-3-(4,6-dimethoxypyrimidine-2-yl)-2-methylindole

To 80 ml of toluene were added 8.0 g (40 m moles) of 1-(4,6-dimethoxypyrimidine-2-yl)-2-propanone and 7.9 g (44 m moles) of 4-chlorophenylhydrazine hydrochloride. Thereto was added 6.54 g (48 m moles) of zinc chloride. Refluxing was made for 2 hours with heating. The reaction mixture was allowed to cool. Then, ethyl acetate and water were added to dissolve the whole reaction mixture. The organic layer was washed with water, separated, and dried over Glauber's salt. The resulting organic layer was concentrated under reduced pressure using a rotary evaporator to obtain an orange solid. The solid was washed with isopropyl ether to obtain 10.2 g (33.7 m moles) of 5-chloro-3-(4,6-dimethoxypyrimidine-2-yl)-2-methylindole. Yield: 84% Melting point: 179 to 181° C.

MS m/e: 303 (M$^+$)

$^1$H-NMR (CDCl$_3$/TMS), δ (ppm):

2.91 (s, 3H), 4.04 (s, 6H), 5.82 (s, 1H), 7.1 (m, 1H), 7.3 (m, 1H), 8.7 (m, 1H)

IR (KBr, cm$^{-1}$): 3510 (NH), 1580

Example 26

Step 2

Production of 4-chloro-2-(4,6-dimethoxypyrimidine-2-ylcarbonyl)acetanilide

In a reactor were placed 6.1 g (20 m moles) of 5-chloro-3-(4,6-dimethoxypyrimidine-2-yl)-2-methylindole, 200 ml of acetone and 100 ml of water. Thereto were added 19.0 g (120 m moles) of potassium permanganate and 8.6 g (40 m moles) of sodium periodate. A reaction was conducted at room temperature for 16 hours. After the completion of the reaction, filtration was made. The filtrate was extracted with ethyl acetate. The ethyl acetate layer was concentrated. The concentrate was purified by silica gel column chromatography (n-hexane/ethyl acetate=4/1) to obtain 1.8 g (5.4 m moles) of 4-chloro-2-(4,6-dimethoxypyrimidine-2-ylcarbonyl)acetanilide. Yield: 27% Melting point: 142 to 144° C.

MS m/e: 335 (M$^+$)

$^1$H-NMR (CDCl$_3$/TMS), δ (ppm):

2.27 (s, 3H), 3.98 (s, 6H), 6.20 (s, 1H), 7.56 (q, 1H), 7.69 (M, 1H), 8.76 (d, 1H)

IR (KBr, cm$^{-3}$): 3320 (NH), 1700, 1660 (C=O)

Example 27

Step 3

Production of 4-chloro-2-(4,6-dimethoxypyrimidine-2-ylhydroxymethyl)acetanilide

In a reactor were placed 1.00 g (3.0 m moles) of 4-chloro-2-(4,6-dimethoxypyrimidine-2-ylcarbonyl)acetanilide and 20 ml of ethanol. The reactor contents were cooled to 5° C. or less. Thereto was added 0.25 g (6.6 m moles) of sodium borohydride. The mixture was stirred at the same temperature for 1 hour. Then, the temperature was increased to room temperature. After the completion of the reaction, an aqueous ammonium chloride solution was added and the mixture was extracted with ethyl acetate. The organic layer was concentrated. The concentrate was purified by silica gel column chromatography (n-hexane/ethyl acetate=1/1) to obtain 0.69 g (2.0 m moles) of 4-chloro-2-(4,6-dimethoxypyrimidine-2-ylhydroxymethyl) acetanilide. Yield: 68%

Melting point: 121 to 123° C.

$^1$H-NMR (CDCl$_3$/TMS), δ (ppm):

2.22 (s, 3H), 3.98 (s, 6H), 4.89 (d, 1H), 5.81 (d, 1H), 5.89 (s, 1H), 7.2 (m, 1H), 7.5 (m, 1H), 7.8 (d, 1H), 9.72 (b, 1H)

IR (KBr, cm$^{-1}$): 3430 (NH), 3300 (OH), 1700, 1600 (C=O)

Example 28

Step 1

Production of 3-(4,6-dimethoxypyrimidine-2-yl)-5-methoxy-2-methylindole

To 80 ml of toluene were added 8.0 g (40 m moles) of 1-(4,6-dimethoxypyrimidine-2-yl)-2-propanone and 7.7 g (44 m moles) of 4-metoxyphenylhydrazine hydrochloride. Thereto was added 6.0 g (44 m moles) of zinc chloride. Refluxing was made for 2 hours with heating. The reaction mixture was allowed to cool. Thereto were added ethyl acetate and water to dissolve the whole reaction mixture. The oily layer was washed with water, separated and dried over Glauber's salt. The resulting organic layer was concentrated under reduced pressure using an rotary evaporator to obtain, as an orange solid, 8.0 g (26.7 m moles) of 3-(4,6-dimethoxypyrimidine-2-yl)-5-methoxy-2-methylindole. Yield: 67% Recrystallization from toluene was made.

Melting point: 182 to 184° C.
MS m/e: 299 ($M^+$.)
$^1$H-NMR (CDCl$_3$/TMS), δ (ppm):
2.87 (s, 3H), 3.89 (s, 3H), 4.07 (s, 6H), 5.84 (s, 1H), 6.9 (m, 1H), 7.2 (m, 1H), 8.2 (b, 1H), 8.7 (s, 1H)
IR (cm$^{-1}$): 3340 (NH), 1570

Example 29

Step 2
Production of 2-(4,6-dimethoxypyrimidine-2-ylcarbonyl)-4-methoxyacetanilide In a reactor were placed 6.0 g (20 m moles) of 3-(4,6-dimethoxypyrimidine-2-yl)-5-methoxy-2-methylindole, 200 ml of acetone and 100 ml of water. Thereto were added 19.0 g (120 m moles) of potassium permanganate and 8.6 g (40 m moles) of sodium periodate. A reaction was conducted at room temperature for 16 hours. After the completion of the reaction, filtration was made. The filtrate was extracted with ethyl acetate. The ethyl acetate layer was concentrated. The residue was purified by silica gel column chromatography (n-hexane/ethyl acetate=4/1) to obtain 0.9 g (2.7 m moles) of 2-(4,6-dimethoxypyrimidine-2-ylcarbonyl)-4-methoxyacetanilide. Yield: 14%

MS m/e: 331 ($M^+$)
$^1$H-NMR (CDCl$_3$/TMS), δ (ppm):
2.25 (s, 3H), 3.74 (s, 3H), 3.96 (s, 6H), 6.17 (s, 1H), 7.1 to 7.2 (m, 2H), 8.7 (d, 1H)
IR (cm$^{-1}$): 3250 (NH), 1690, 1650 (C=O)

Example 30

Step 3
Production of 2-(4,6-dimethoxypyrimidine-2-ylhydroxymethyl)-4-methoxyacetanilide In a reactor were placed 0.66 g (2.0 m moles) of 2-(4,6-dimethoxypyrimidine-2-ylcarbonyl)-4-methoxyacetanilide and 10 ml of ethanol. The reactor contents were cooled to 5° C. or less. Thereto was added 0.17 g (4.4 m moles) of sodium borohydride. The mixture was stirred at the same temperature for 1 hour. Then, the mixture was heated to room temperature. After the completion of the reaction, an aqueous ammonium chloride solution was added and extraction with ethyl acetate was conducted. The organic layer was concentrated. The concentrate was purified by silica gel column chromatography (n-hexane/ethyl acetate=2/3) to obtain 0.55 g (1.6 m moles) of 2-(4,6-dimethoxypyrimidine-2-ylhydroxymethyl)-4-methoxyacetanilide. Yield: 82%

Melting point: 122° C. to 125° C.
$^1$H-NMR (CDCl$_3$/TMS), δ (ppm):
2.21 (s, 3H), 3.80 (s, 3H), 3.97 (s, 6H), 4.87 (d, 1H), 5.84 (d, 1H), 5.96 (s, 1H), 6.8 (m, 1H), 7.07 (d, 1H), 7.69 (q, 1H), 9.49 (b, 1H)
IR (cm$^{-1}$): 3470 (NH), 3250 (OH), 1670, 1600 (C=O)

Example 31

Step 6

Production of 2-(4,6-dimethoxypyrimidine-2-ylhdroxymethyl)-6-methoxymethylaniline In a reactor were placed 1.0 g (0.0033 moles) of 2-(4,6-dimethoxypyrimidine-2-yl)carbonyl-6-methoxymethylaniline and 50 ml of ethanol. Thereto was added, with ice-cooling (10° C. or less), 0.125 g (0.0033 moles) of sodium borohydride. The mixture was stirred at room temperature for 2 hours. To the mixture after reaction was added a saturated aqueous ammonium chloride solution to make the mixture acidic. Then, ethyl acetate was added for extraction. The organic layer was washed with water and a saturated aqueous sodium chloride solution in this order. Then, the organic layer was dried with anhydrous sodium sulfate and concentrated to obtain 0.91 g (0.0030 moles) of 2-(4,6-dimethoxypyrimidine-2-ylhdroxymethyl)-6-methoxymethylaniline.

Yield: 900. The obtained 2-(4,6-dimethoxypyrimidine-2-ylhdroxymethyl)-6-methoxymethylaniline was subjected to instrumental analysis, and the data agreed to those of the compounds obtained in Examples.

INDUSTRIAL APPLICABILITY

According to the present invention there are provided a 2-(pyrimidine-2-ylhydroxymethyl)acetanilide compound which is an important intermediate for a sulfonanilide compound showing an excellent herbicidal effect, and an industrial process for producing a substituted aniline compound using the above acetanilide compound as an intermediate.

What is claimed is:
1. 2-Methoxymethylphenylhydrazine.

* * * * *